US009380973B2

(12) United States Patent
Fletcher et al.

(10) Patent No.: US 9,380,973 B2
(45) Date of Patent: Jul. 5, 2016

(54) BIOLOGICAL FLUID SAMPLING TRANSFER DEVICE AND BIOLOGICAL FLUID SEPARATION AND TESTING SYSTEM

(71) Applicant: Becton, Dickinson and Company, Franklin Lakes, NJ (US)

(72) Inventors: Gary D. Fletcher, Sparta, NJ (US); Craig A. Gelfand, Jackson, NJ (US); Bradley M. Wilkinson, North Haledon, NJ (US); Daniel J. Marchiarullo, Morris Plains, NJ (US); Ashley Rachel Rothenberg, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/251,720

(22) Filed: Apr. 14, 2014

(65) Prior Publication Data

US 2014/0308167 A1 Oct. 16, 2014

Related U.S. Application Data

(60) Provisional application No. 61/811,918, filed on Apr. 15, 2013.

(51) Int. Cl.
*A61B 5/15* (2006.01)
*G01N 33/49* (2006.01)
(Continued)

(52) U.S. Cl.
CPC ......... *A61B 5/150213* (2013.01); *A61B 5/1411* (2013.01); *A61B 5/151* (2013.01);
(Continued)

(58) Field of Classification Search
CPC .............. A61B 5/150213; A61B 5/15144; A61B 5/15105; A61B 5/157; A61B 5/150267; A61B 5/151; A61B 5/150343; A61B 5/15101; A61B 5/150748; G01N 1/34; G01N 33/5002; G01N 1/4005; G01N 1/4077; B01L 3/5021
See application file for complete search history.

(56) References Cited

U.S. PATENT DOCUMENTS 3,322,114 A 5/1967 Portnoy et al.
3,640,393 A 2/1972 Hurtig
(Continued)

FOREIGN PATENT DOCUMENTS

CN 1382966 A 12/2002
CN 101102847 A 1/2008
(Continued)

OTHER PUBLICATIONS

Membrane Separation Technology for Research and Quality Control, Sartorius AG, Separation Technology, Laboratory Filtration; Mar. 1, 1997.

*Primary Examiner* — Lore Jarrett
(74) *Attorney, Agent, or Firm* — The Webb Law Firm

(57) ABSTRACT

A biological fluid sampling transfer device that is adapted to receive and separate a multi-component blood sample is disclosed. After separation, the biological fluid sampling transfer device is able to transfer a plasma portion of the blood sample to a point-of-care testing device. The biological fluid sampling transfer device of the present disclosure also provides a closed sampling and transfer system that reduces the exposure of a blood sample and provides fast mixing of a blood sample with an anticoagulant. The biological fluid sampling transfer device is engageable with a blood testing device for closed transfer of a portion of the plasma portion from the biological fluid sampling transfer device to the blood testing device. The blood testing device is adapted to receive the plasma portion to analyze the blood sample and obtain test results.

21 Claims, 6 Drawing Sheets

(51) Int. Cl.
  *A61M 1/34* (2006.01)
  *G01N 1/28* (2006.01)
  *G01N 1/40* (2006.01)
  *G01N 1/34* (2006.01)
  *B01L 3/00* (2006.01)
  *B04B 7/08* (2006.01)
  *A61B 5/151* (2006.01)
  *A61B 5/157* (2006.01)

(52) U.S. Cl.
  CPC .......... *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | 4/1985 | Nielsen et al. | |
| 4,627,445 A | 12/1986 | Garcia et al. | |
| 5,055,203 A | 10/1991 | Columbus | |
| 5,163,442 A | 11/1992 | Ono | |
| 5,219,999 A | 6/1993 | Suzuki et al. | |
| 5,422,018 A | 6/1995 | Saunders et al. | |
| 5,636,640 A | 6/1997 | Staehlin | |
| 5,726,026 A | 3/1998 | Wilding et al. | |
| 5,839,715 A | 11/1998 | Leinsing | |
| 5,922,591 A | 7/1999 | Anderson et al. | |
| 6,074,183 A | 6/2000 | Allen et al. | |
| 6,264,619 B1 | 7/2001 | Ferguson | |
| 6,506,167 B1 | 1/2003 | Ishimito et al. | |
| 6,869,405 B2 | 3/2005 | Marsden | |
| 8,158,410 B2 | 4/2012 | Tang et al. | |
| 2002/0009015 A1 | 1/2002 | Laugharn, Jr. et al. | |
| 2002/0143298 A1 | 10/2002 | Marsden | |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0214927 A1 | 9/2005 | Haley | |
| 2006/0029923 A1 | 2/2006 | Togawa et al. | |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2010/0089815 A1 | 4/2010 | Zhang et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0124130 A1 | 5/2011 | Wagner et al. | |
| 2011/0124984 A1 | 5/2011 | Rostaing | |
| 2012/0152858 A1 | 6/2012 | Yang | |
| 2012/0275955 A1 | 11/2012 | Haghgooie et al. | |
| 2012/0277696 A1 | 11/2012 | Gonzalez-Zugasti et al. | |
| 2012/0277697 A1 | 11/2012 | Haghgooie et al. | |
| 2013/0026085 A1 | 1/2013 | Samsoondar | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101332320 A | 12/2008 |
| CN | 102429665 A | 5/2012 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

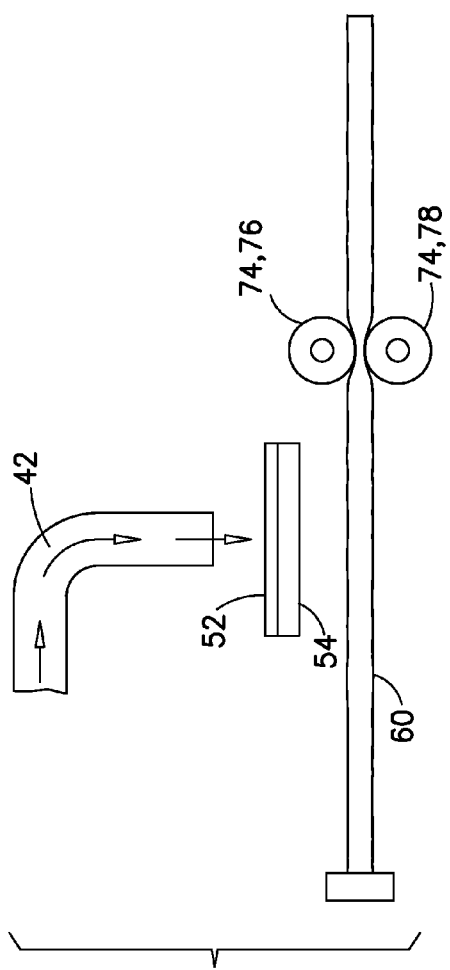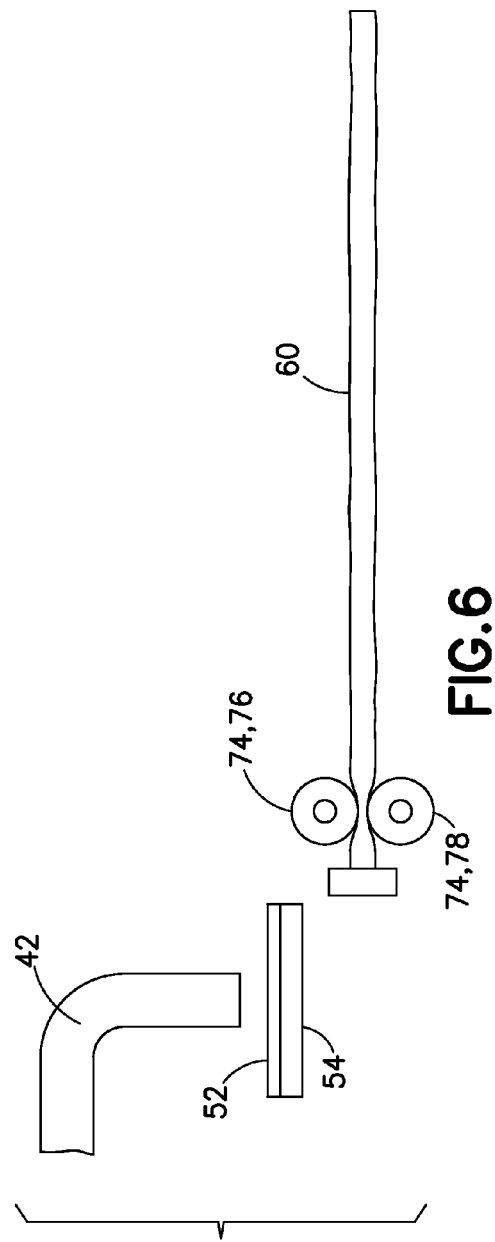

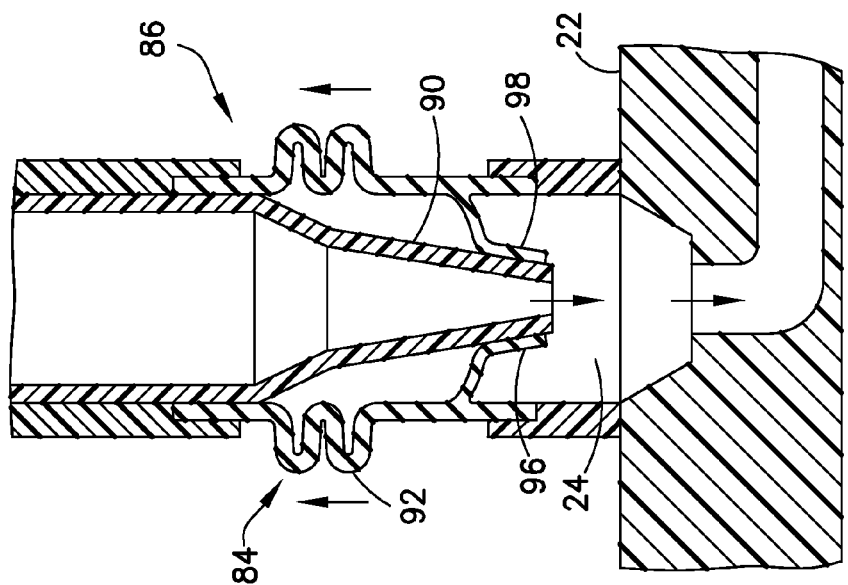
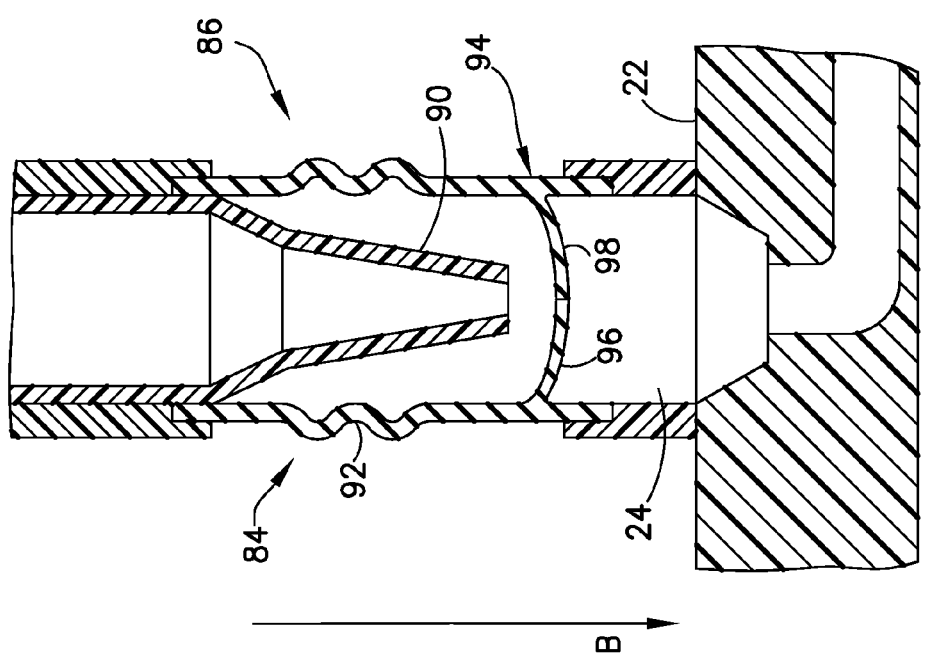

BIOLOGICAL FLUID SAMPLING TRANSFER DEVICE AND BIOLOGICAL FLUID SEPARATION AND TESTING SYSTEM

CROSS REFERENCE TO RELATED APPLICATIONS

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid sampling transfer device, such as a blood sampling transfer device, that is adapted to receive a multi-component fluid. After collecting the fluid sample, such as a blood sample, the sampling transfer device is able to separate at least one component of the sample from at least another component of the sample, such as the plasma portion from the cellular portion. After separation, the sampling transfer device is able to transfer the plasma portion of the blood sample to a point-of-care testing device. The sampling transfer device of the present disclosure also provides a closed sampling and transfer system that reduces the exposure of a blood sample and provides fast mixing of a blood sample with a sample stabilizer, such as an anticoagulant. The sampling transfer device is engageable with a blood testing device for closed transfer of a portion of the plasma portion from the sampling transfer device to the blood testing device. The blood testing device is adapted to receive the plasma portion to analyze the blood sample and obtain test results.

Some of the advantages of the sampling transfer device and the biological fluid separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The sampling transfer device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

In accordance with an embodiment of the present invention, a biological fluid sampling transfer device adapted to receive a multi-component blood sample includes a housing having an inlet port and an outlet port, the inlet port and the outlet port in fluid communication. The biological fluid sampling and transfer device also includes a filter disposed between the inlet port and the outlet port, the filter adapted to restrain at least a first part of the multi-component blood sample, and to allow at least a second part of the multi-component blood sample to pass therethrough. The biological fluid and sampling device also includes a compression element disposed between the inlet port and the outlet port, the compression element spaced from the filter; and a holding element movable within the housing between a first position, in which the holding element receives the second part of the multi-component blood sample from the filter, and a second position, in which the compression element is adapted to direct the second part of the multi-component blood sample from the holding element to the outlet port.

In certain configurations, the first part of the multi-component blood sample is a cellular component and the second part of the multi-component blood sample is a plasma component. In other configurations, the compression element provides a force to the holding element to expel the second part of the multi-component blood sample therefrom. Optionally, the compression element may include a pair of rollers configured to squeeze the second part of the multi-component blood sample from the holding element. The filter may include a lateral flow membrane. Optionally, a sample stabilizer may be disposed between the filter and the inlet port.

In additional configurations, the holding element may include a wicking membrane. A vent element may also be disposed within the housing, with the vent element in communication with the inlet port. Optionally, the outlet port may include a septum transitionable between a closed position and an open position. The outlet port may be adapted for connection to a point-of-care testing device for closed transfer of a portion of the second part of the multi-component blood sample from the blood sampling transfer device to the point-of-care testing device via the outlet port.

In accordance with another embodiment of the present invention, a biological fluid separation and testing system, such as a blood separation and testing system, for a multi-component blood sample includes a biological fluid sampling transfer device, such as a blood sampling transfer device, adapted to receive the multi-component blood sample. The blood sampling transfer device includes a housing having an inlet port and an outlet port, with the inlet port and the outlet port in fluid communication. The blood sampling transfer device also includes a filter disposed between the inlet port and the outlet port, the filter adapted to restrain at least a first part of the multi-component blood sample, and to allow at least a second part of the multi-component blood sample to pass therethrough. The blood sampling transfer device also includes a compression element disposed between the inlet port and the outlet port, the compression element spaced from the filter, and a holding element movable within the housing between a first position, in which the holding element receives the second part of the multi-component blood sample from the filter, and a second position, in which the compression element is adapted to direct the second part of the multi-component blood sample from the holding element to the outlet port. The biological fluid separation and testing system also includes a blood testing device having a receiving port engageable with the outlet port of the housing of the blood sampling transfer device for closed transfer of a portion of the second part of the multi-component blood sample from the blood sampling transfer device to the blood testing device via the outlet port.

In certain configurations, the first part of the multi-component blood sample is a cellular component and the second part of the multi-component blood sample is a plasma component. The blood testing device may include a point-of-care testing device. Optionally, the compression element provides a force to the holding element to expel the second part of the multi-component blood sample therefrom. The compression element may include a pair of rollers configured to squeeze the second part of the multi-component blood sample from the holding element. The filter may include a lateral flow membrane.

In other configurations, the system may also include a sample stabilizer disposed between the filter and the inlet port. The holding element may include a wicking membrane. In still other configurations, the system may include a vent element disposed within the housing, with the vent element in communication with the inlet port. The outlet port may include a septum transitionable between a closed position and an open position. Further, the filter may include a fibrous membrane.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 5 is a schematic representation of a holding element of a biological fluid sampling transfer device in a first position in accordance with an embodiment of the present invention.

FIG. 6 is a schematic representation of a holding element of a biological fluid sampling transfer device in a second position in accordance with an embodiment of the present invention.

FIG. 7 is a cross-sectional view of a septum of a biological fluid sampling transfer device in accordance with an embodiment of the present invention, with the septum in a closed position.

FIG. 8 is a cross-sectional view of a septum of a biological fluid sampling transfer device in accordance with an embodiment of the present invention, with the septum in an open position.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
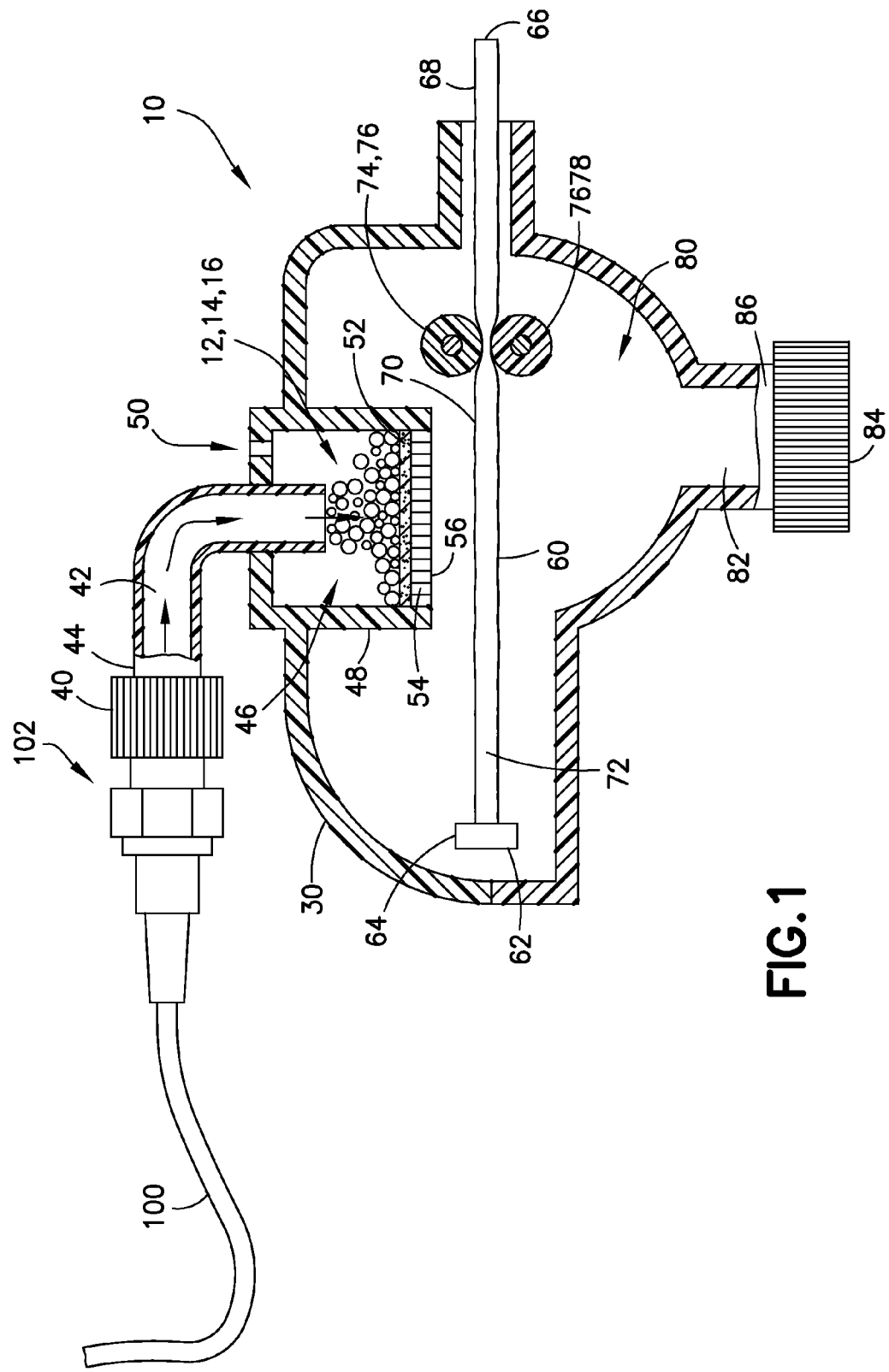
FIG. 1 is a cross-sectional view of a biological fluid sampling transfer device in accordance with an embodiment of the present invention, with a biological fluid collection device attached to the biological fluid sampling transfer device.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge requiring repeat testing, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

Figure 2:
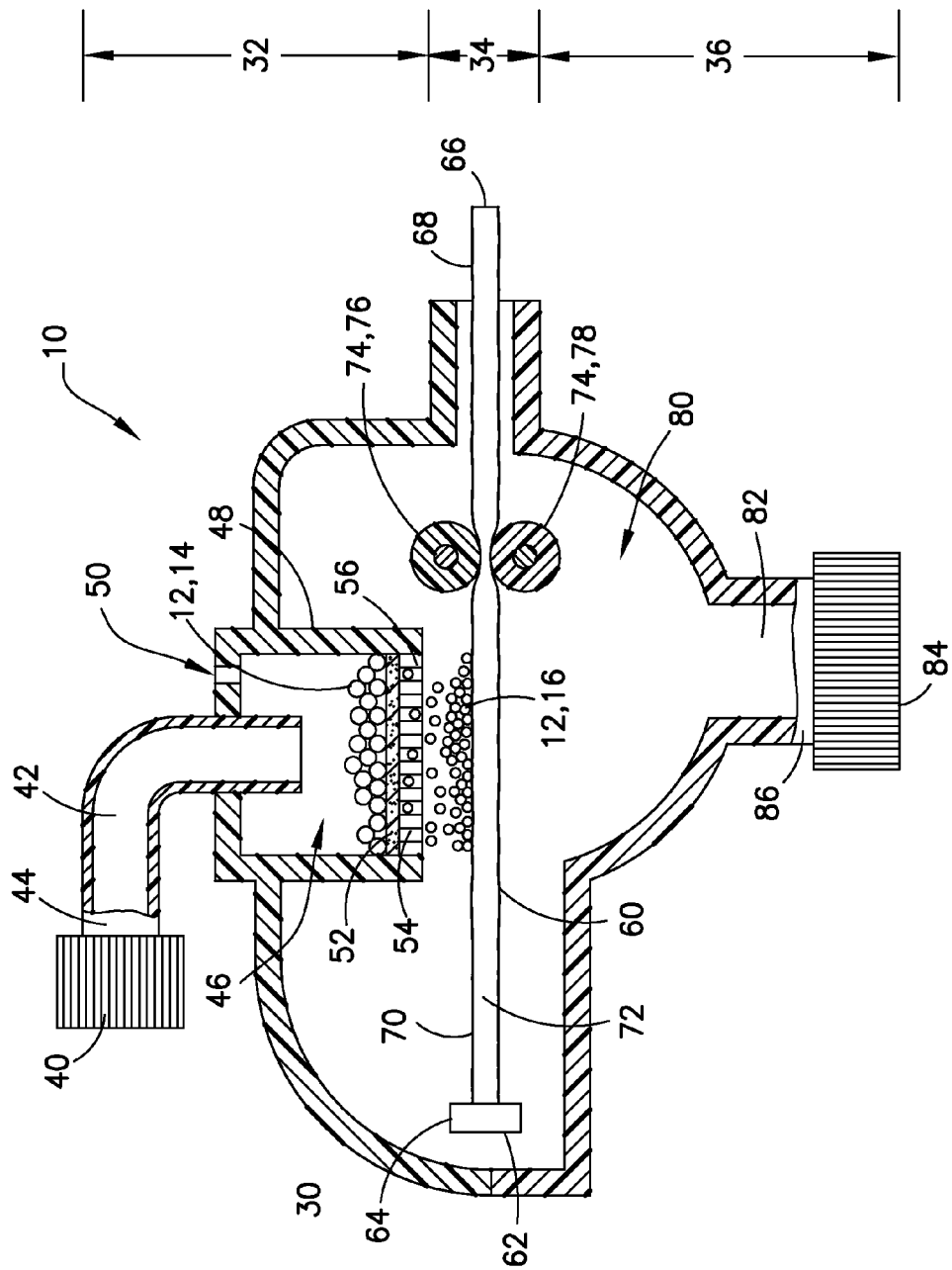
FIG. 2 is a cross-sectional view of a biological fluid sampling transfer device in accordance with an embodiment of the present invention, with a holding element of the biological fluid sampling transfer device in a first position.
Figure 3:
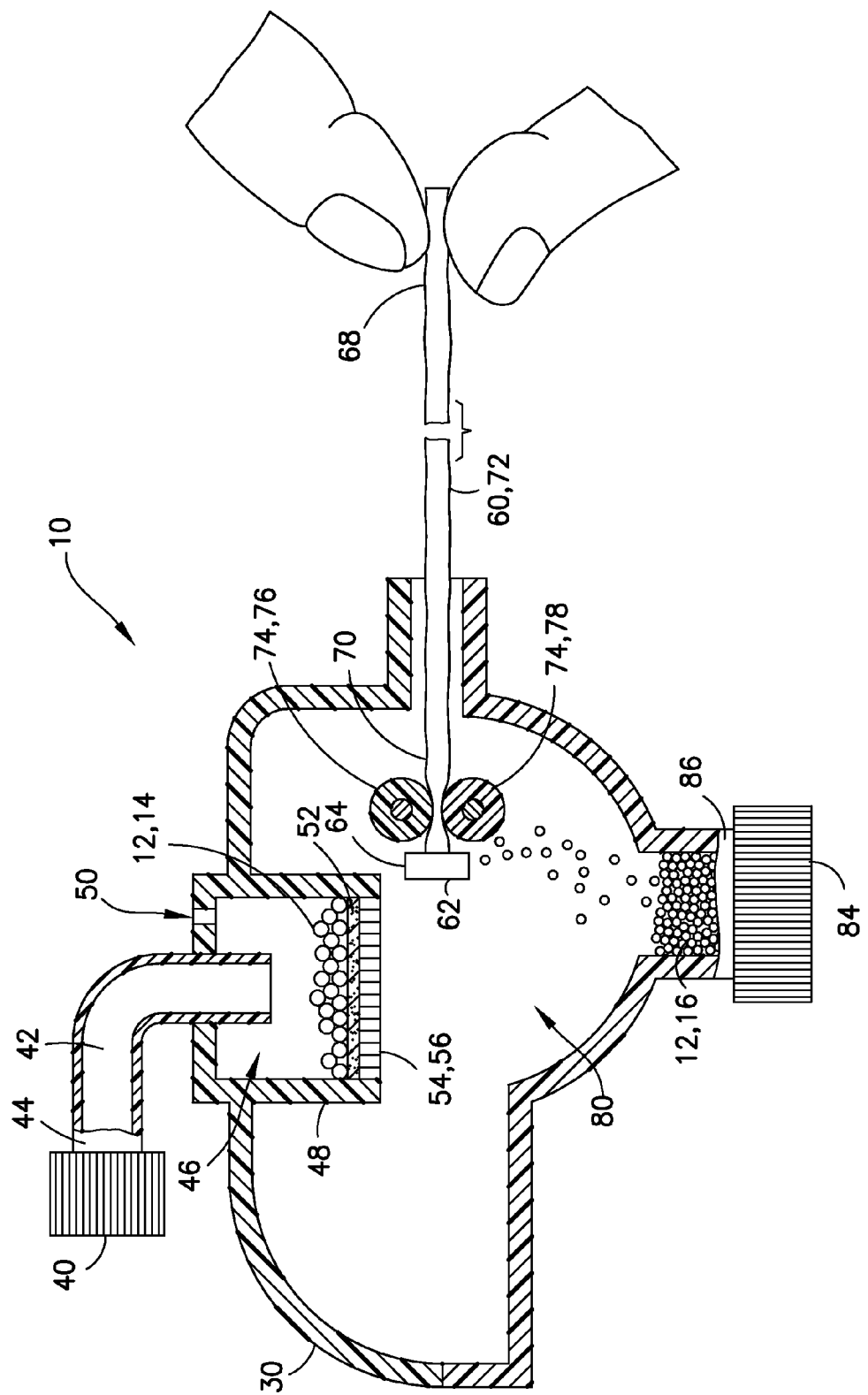
FIG. 3 is a cross-sectional view of a biological fluid sampling transfer device in accordance with an embodiment of the present invention, with a user pulling a holding element of the biological fluid sampling transfer device to a second position.

FIGS. 1-3 illustrate an exemplary embodiment of the present disclosure. Referring to FIGS. 1-3, a biological fluid sampling transfer device 10, such as a blood sampling transfer device, of the present disclosure is adapted to receive a multi-component blood sample 12 having, for example, a cellular portion 14 and a plasma portion 16. After collecting the blood sample 12, the blood sampling transfer device 10 is able to separate the plasma portion 16 from the cellular portion 14. After separation, the blood sampling transfer device 10 is able to transfer the plasma portion 16 of the blood sample 12 to a point-of-care testing device. The blood sampling transfer device 10 of the present disclosure also provides a closed sampling and transfer system that reduces the exposure of a blood sample and provides fast mixing of a blood sample with a sample stabilizer, such as a preservative, an anticoagulant, or a substance for preserving a specific element within the blood sample, such as RNA or a protein analyte.

Figure 4:
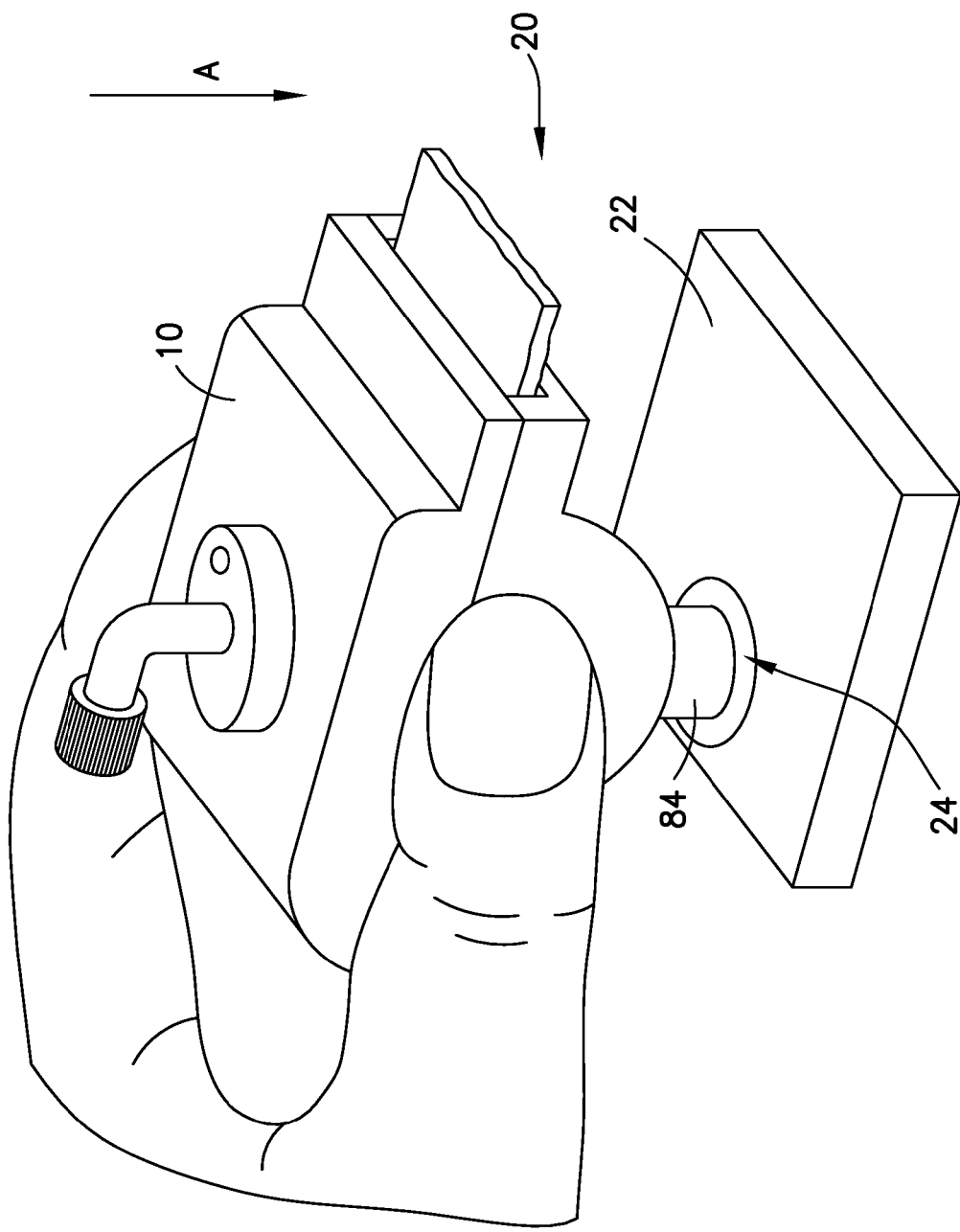
FIG. 4 is a perspective view of a biological fluid separation and testing system in accordance with an embodiment of the present invention.

FIG. 4 illustrates an exemplary embodiment of the present disclosure. Referring to FIG. 4, a biological fluid separation and testing system 20, such as a blood separation and testing system, of the present disclosure includes a blood sampling transfer device 10 and a blood testing device 22 engageable with the blood sampling transfer device 10 for closed transfer of a portion of the plasma portion 16 (FIG. 3) from the blood sampling transfer device 10 to the blood testing device 22. The blood testing device 22 is adapted to receive the plasma portion 16 to analyze the blood sample and obtain test results.

The blood sampling transfer device of the present disclosure enables integrated blood collection and plasma creation in a closed system without centrifugation. The clinician may collect and separate the blood sample and then immediately transfer the plasma portion to the point-of-care testing device 22 without further manipulation. This enables collection and transfer of plasma to the point-of-care testing device 22 without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

Referring to FIGS. 1-4, a blood sampling transfer device 10 generally includes a housing 30 having an upper portion 32, a middle portion 34, and a lower portion 36. The housing 30 of the blood sampling transfer device 10 is adapted to receive a blood sample 12 therein. The blood sample 12 may include a cellular portion 14 and a plasma portion 16. The housing 30 includes a first chamber 46 and a second chamber 80. The housing 30 includes an inlet port 40 and an outlet port or transfer port 84. The inlet port 40 and the outlet port 84 are in fluid communication in the manner described below. The upper portion 32 of the housing 30 generally includes an inlet port 40, an inlet channel 42, a septum 44 at the inlet port 40, a first chamber 46 defined by first chamber walls 48 and including a venting port 50, a layer of sample stabilizer 52, and a filter 54.

The inlet port 40 is adapted to be connected to a blood collection set 100 to allow for the collection of a blood sample 12 into the blood sampling transfer device 10. The inlet port 40 may be sized and adapted for engagement with a separate device, such as a needle assembly or IV connection assembly and, therefore, may include a mechanism for such engagement as is conventionally known. For example, in one embodiment, the inlet port 40 may include a luer lock or luer tip for engagement with an optional separate luer mating component of such a separate device for attachment therewith. For example, referring to FIG. 1, the blood collection set 100 may include a luer component 102 for engagement with inlet port 40 of blood sampling transfer device 10. In this manner, the inlet port 40 is connectable to the blood collection set 100 for the collection of a blood sample into the blood sampling transfer device 10. In addition, a mechanism for locking engagement between the inlet port 40 and the blood collection set 100 may also be provided. Such luer connections and luer locking mechanisms are well known in the art. The blood collection set 100 may include a needle assembly, an IV connection assembly, a PICC line, an arterial indwelling line, or similar blood collection means.

Referring to FIGS. 1-3, the inlet port 40 is in fluid communication with the first chamber 46 via the inlet channel 42. The inlet port 40 may also include a resealable septum 44 that is transitionable between a closed position and an open position. With the septum 44 in an open position, a blood sample 12 may flow through the inlet port 40 to the first chamber 46 via the inlet channel 42 as shown in FIG. 1. The first chamber 46 is defined by the first chamber walls 48 as shown in FIGS. 1-3. The first chamber 46 is sealed such that a cellular portion 14 of the blood sample 12 is contained within the first chamber 46 and the plasma portion 16 of the blood sample 12 can exit the first chamber 46 by passing through the filter 54 to the second chamber 80 as discussed below. Only the plasma portion 16 of the blood sample 12 is able to pass through the filter 54. In one embodiment, the first chamber 46 includes a venting port 50 that allows for a blood sample to flow through the inlet port 40 to the first chamber 46 of the housing 30 of the blood sampling transfer device 10 via venous or arterial pressure. In other embodiments, the blood sampling transfer device 10 may include other vent elements disposed within the housing 30 and in communication with the inlet port 40 to allow a blood sample to flow through the inlet port 40 to the first chamber 46 of the housing 30. The first chamber 46 also includes a layer of sample stabilizer 52. In one embodiment, the layer of sample stabilizer 52 may be disposed over the filter 54. In other embodiments, the layer of sample stabilizer 52 may be located anywhere between the inlet port 40 and the filter 54. In this manner, as a blood sample 12 flows through the inlet port 40 and into the first chamber 46, the blood sampling transfer device 10 provides passive and fast mixing of the blood sample 12 with the sample stabilizer 52.

The first chamber walls 48 includes a filter 54 disposed between the first chamber 46 and the second chamber 80 of the lower portion 36 as shown in FIGS. 1-3. The filter 54 is adapted to trap the cellular portion 14 of the blood sample 12 within the first chamber 46 and allow the plasma portion 16 of the blood sample 12 to pass through the filter 54 to the second chamber 80 of the lower portion 36 as shown in FIG. 2 and as discussed in more detail below. In one embodiment, the filter 54 includes a lateral flow membrane 56. In one embodiment, the filter 54 may be either hollow fiber membrane filters or flat membrane filters, such as track-etch filters. Membrane filter pore size and porosity can be chosen to optimize separation of clean (i.e., red blood cell free, white blood cell free, and/or platelet free) plasma in an efficient manner. In other embodiments, the filter 54 may comprise any filter that is able to trap the cellular portion 14 of the blood sample 12 within the first chamber 46 and allow the plasma portion 16 of the blood sample 12 to pass through the filter 54 to the second chamber 80 of the lower portion 36 as shown in FIG. 2.

The middle portion 34 of the housing 30 generally includes a holding element 60, a compression element 74, and a portion of the second chamber 80. The holding element 60 is movable within the housing 30 of the blood sampling transfer device 10 between a first position (FIGS. 1, 2, and 5), in which the holding element 60 receives the plasma portion 16 of the blood sample 12 from the filter 54, and a second position (FIGS. 3 and 6), in which the compression element 74 is adapted to direct the plasma portion 16 of the blood sample 12 from the holding element 60 to the outlet port 84. The holding element 60 generally includes a first end 62 having a barrier portion 64, a second end 66 having a handle portion 68, and a holding portion or body portion 70 extending between the first end 62 and the second end 66. The handle portion 68 extends from the housing 30 so that a clinician or user may grasp the holding element 60 to move the holding element 60 between the first position (FIGS. 1, 2, and 5) and the second position (FIGS. 3 and 6). The barrier portion 64 provides an area that prevents the holding element 60 from being removed from the housing 30 of the blood sampling transfer device 10. For example, the barrier portion 64 may include an increased width portion as shown in FIGS. 1-6. In this manner, with the holding element 60 in the second position, the increased width portion provides a physical barrier that contacts the compression element 74 and prevents the holding element 60 from being removed from the housing 30 of the blood sampling transfer device 10 as shown in FIG. 3. In an alternate embodiment, the holding element 60 may be removed from the blood sampling transfer device 10 for further testing. In one embodiment, the holding element 60 is spaced away from the filter 54 to allow room for a "squeegee" effect and the barrier portion 64 to pass by and prevent complete removal. In another embodiment, the holding element 60 may be adjacent the filter 54.

The holding or body portion 70 provides an area to receive the plasma portion 16 of the blood sample 12 as shown in FIG. 2. In one embodiment, the holding element 60 includes a wicking membrane 72. In other embodiments, the holding element 60 may comprise any element that is able to receive the plasma portion 16 of the blood sample 12 and move within the housing 30 to communicate with the compression element 74 to direct the plasma portion 16 to the outlet port 84 as discussed in more detail below. The holding element 60 is deformable such that the compression element 74 can exert a force on or squeeze the holding element 60 to direct the plasma portion 16 to the outlet port 84 as discussed below.

The compression element 74 is disposed within the housing 30 between the inlet port 40 and the outlet port 84 as shown in FIGS. 1-3. In one embodiment, the compression element 74 is spaced a distance from the filter 54 so that when the holding element 60 moves from the first position to the second position, the increased width portion or barrier portion 64 of the holding element 60 is able to pass under the filter 54 and the first chamber 46 as shown in FIG. 3. The compression element 74 provides a force to the holding element 60 to expel the plasma portion 16 from the holding element 60 as shown in FIG. 3 and as described in more detail below. In one embodiment, the compression element 74 comprises a pair of rollers 76, 78 configured to squeeze the plasma portion 16 from the holding element 60 as shown in FIG. 3.

The lower portion 36 of the housing 30 generally includes a portion of the second chamber 80, an outlet channel 82, an outlet port or transfer port 84, and a valve or septum 86 (FIGS. 7 and 8) at the outlet port 84. The outlet port 84 is adapted for connection to a point-of-care testing device 22 for closed transfer of a portion of the plasma portion 16 from the blood sampling transfer device 10 to the point-of-care testing device 22 via the outlet port 84 as described in more detail below. Referring to FIGS. 1-3, the outlet port 84 is in fluid communication with the second chamber 80 via the outlet channel 82. The outlet port 84 may also include a valve or septum 86 that is transitionable between a closed position (FIG. 7) and an open position (FIG. 8). With the valve or septum 86 in an open position (FIG. 8), the plasma portion 16 of the blood sample 12 may flow through the outlet port 84 to a blood testing device or a point-of-care testing device 22 (FIG. 4).

Referring to FIG. 4, a blood testing device or point-of-care testing device 22 includes a receiving port 24 adapted to receive the outlet port 84 of the blood sampling transfer device 10. The blood testing device 22 is adapted to receive the outlet port 84 of the blood sampling transfer device 10 for closed transfer of a portion of the plasma portion 16 (FIG. 3) from the blood sampling transfer device 10 to the blood testing device 22. The blood testing device 22 is adapted to receive the plasma portion 16 to analyze the blood sample and obtain test results.

As discussed above, the outlet port 84 of the blood sampling transfer device 10 may include a valve or septum 86 that is transitionable between a closed position and an open position. With the valve or septum 86 in an open position, the plasma portion 16 of the blood sample 12 may flow through the outlet port 84 to a blood testing device or a point-of-care testing device 22 (FIG. 4).

In one embodiment, referring to FIGS. 7 and 8, the valve 86 may generally include a transfer channel 90, a bellows or deformable wall member 92, and a septum or barrier 94 having a first barrier wall 96 and a second barrier wall 98. Referring to FIG. 7, the valve 86 is in a closed position to prevent the plasma portion 16 of the blood sample 12 from flowing through the outlet port 84. In this manner, the plasma portion 16 is sealed within the blood sampling transfer device 10. Referring to FIG. 8, the valve 86 is in an open position so that the plasma portion 16 of the blood sample 12 may flow through the outlet port 84 to a blood testing device or a point-of-care testing device 22 (FIG. 4).

Referring to FIG. 7, with the plasma portion 16 received within the outlet channel 82 of the blood sampling transfer device 10 (FIG. 3), the outlet port 84 of the blood sampling transfer device 10 is then positioned over the receiving port 24 of the point-of-care testing device 22. Pushing down in the direction of arrow B compresses the deformable wall member 92 and opens up the first barrier wall 96 and the second barrier wall 98 of the septum 94 as shown in FIG. 8. With the valve 86 in the open position, the plasma portion 16 of the blood sample 12 is allowed to flow through the receiving port 24 to the point-of-care testing device 22 in a closed manner reducing exposure to the clinician and the patient.

The valve 86 of the blood sampling transfer device 10 only opens when the outlet port 84 is pressed upon the receiving port 24 of the point-of-care testing device 22. This releases the isolated plasma portion 16 directly into the receiving port 24 of the point-of-care testing device 22, thus mitigating unnecessary exposure to the patient's blood.

Referring to FIGS. 1-4, use of a blood sampling transfer device of the present disclosure will now be described. Referring to FIG. 1, the inlet port 40 of the blood sampling transfer device 10 is adapted to be connected to a blood collection set 100 to allow for the collection of a blood sample 12 into the blood sampling transfer device 10 as discussed above. Once the blood collection set 100 is connected to a patient and the resealable septum 44 of the inlet port 40 is in the open position, blood begins to flow from the blood collection set 100 through the inlet port 40 to the first chamber 46 via the inlet channel 42 due to the venting port 50 that allows flow via venous or arterial pressure. As the blood sample 12 slowly fills the blood sampling transfer device 10, it is collected and stabilized over a layer of sample stabilizer 52.

Referring to FIG. 2, the plasma portion 16 of the blood sample 12 may then flow through the filter 54 so that the plasma portion 16 is separated from the cellular portion 14. The plasma portion 16 passes through the filter 54 and is deposited onto the holding element 60 such that the holding element 60 contains the plasma portion 16. After disconnecting the blood sampling transfer device 10 from the blood collection set 100 or other blood collection line, the blood sampling transfer device 10 is held with one hand and with the other hand the clinician pulls out the holding element 60 as shown in FIG. 3. As the clinician pulls the holding element 60 from the first position to the second position, it passes through a pair of rollers 76, 78 such that the plasma portion 16 is directed toward the outlet channel 82 of the outlet port 84. The compression element 74 or pair of rollers 76, 78 provides a force to the holding element 60 to expel the plasma portion 16 from the holding element 60. In one embodiment, the compression element 74 deforms or squeezes the holding element 60 and a first roller 76 and a second roller 78 contacts the plasma portion 16 to push the plasma portion 16 off the holding element 60 and to the outlet channel 82 of the outlet port 84.

Referring to FIG. 4, the clinician then presses the outlet port 84 against the receiving port 24 of the point-of-care testing device 22 in the direction of arrow A to open the valve 86 (FIG. 8) and to transfer the collected plasma portion 16 to the point-of-care testing device 22. The blood testing device 22 is adapted to receive the outlet port 84 of the blood sampling transfer device 10 for closed transfer of a portion of the plasma portion 16 from the blood sampling transfer device 10 to the blood testing device 22. The blood testing device 22 is adapted to receive the plasma portion 16 to analyze the blood sample and obtain test results.

Some of the advantages of the blood sampling transfer device and the blood separation and testing system of the present disclosure over prior systems are that it is a closed system which reduces blood sample exposure, it provides passive and fast mixing of the blood sample with a sample stabilizer, such as an anticoagulant, it facilitates separation of the blood sample without transferring the blood sample to a separate device, and it is capable of transferring pure plasma to the point-of-care testing device 22. The blood sampling transfer device of the present disclosure enables integrated blood collection and plasma creation in a closed system without centrifugation. The clinician may collect and separate the blood sample and then immediately transfer the plasma portion to the point-of-care testing device 22 without further manipulation. This enables collection and transfer of plasma to the point-of-care testing device 22 without exposure to blood. In addition, the blood sampling transfer device of the present disclosure minimizes process time by processing the blood within the blood sampling transfer device and without external machinery. Further, for tests which only require small amounts of blood, it eliminates the waste associated with blood collection and plasma separation with an evacuated tube.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid sampling transfer device adapted to receive a multi-component blood sample, the biological fluid sampling transfer device comprising:
    a housing having an inlet port and an outlet port, the inlet port and the outlet port in fluid communication;
    a filter disposed between the inlet port and the outlet port, the filter restrains at least a first part of the multi-component blood sample, and allows at least a second part of the multi-component blood sample to pass therethrough;
    a compression element disposed between the inlet port and the outlet port, the compression element spaced from the filter; and
    a holding element movable within the housing between a first position, in which the holding element receives the second part of the multi-component blood sample from the filter, and a second position, in which the compression element contacts a portion of the holding element to direct the second part of the multi-component blood sample from the holding element to the outlet port.

2. The biological fluid sampling transfer device of claim 1, wherein the first part of the multi-component blood sample is a cellular component and the second part of the multi-component blood sample is a plasma component.

3. The biological fluid sampling transfer device of claim 1, wherein the compression element provides a force to the holding element to expel the second part of the multi-component blood sample therefrom.

4. The biological fluid sampling transfer device of claim 1, wherein the compression element comprises a pair of rollers that squeeze the second part of the multi-component blood sample from the holding element.

5. The biological fluid sampling transfer device of claim 1, wherein the filter comprises a lateral flow membrane.

6. The biological fluid sampling transfer device of claim 1, further comprising a sample stabilizer disposed between the filter and the inlet port.

7. The biological fluid sampling transfer device of claim 1, wherein the holding element comprises a wicking membrane.

8. The biological fluid sampling transfer device of claim 1, further comprising a vent element disposed within the housing, the vent element in communication with the inlet port.

9. The biological fluid sampling transfer device of claim 1, wherein the outlet port includes a septum transitionable between a closed position and an open position.

10. The biological fluid sampling transfer device of claim 1, wherein the outlet port is connectable to a point-of-care testing device for closed transfer of a portion of the second part of the multi-component blood sample from the biological fluid sampling transfer device to the point-of-care testing device via the outlet port.

11. A biological fluid separation and testing system for a multi-component blood sample, the biological fluid separation and testing system comprising:
   a biological fluid sampling transfer device adapted to receive the multi-component blood sample, the biological fluid sampling transfer device comprising:
      a housing having an inlet port and an outlet port, the inlet port and the outlet port in fluid communication;
      a filter disposed between the inlet port and the outlet port, the filter restrains at least a first part of the multi-component blood sample, and allows at least a second part of the multi-component blood sample to pass therethrough;
      a compression element disposed between the inlet port and the outlet port, the compression element spaced from the filter; and
      a holding element movable within the housing between a first position, in which the holding element receives the second part of the multi-component blood sample from the filter, and a second position, in which the compression element contacts a portion of the holding element to direct the second part of the multi-component blood sample from the holding element to the outlet port; and
   a blood testing device having a receiving port engageable with the outlet port of the housing of the biological fluid sampling transfer device for closed transfer of a portion of the second part of the multi-component blood sample from the biological fluid sampling transfer device to the blood testing device via the outlet port.

12. The biological fluid separation and testing system of claim 11, wherein the first part of the multi-component blood sample is a cellular component and the second part of the multi-component blood sample is a plasma component.

13. The biological fluid separation and testing system of claim 11, wherein the blood testing device comprises a point-of-care testing device.

14. The biological fluid separation and testing system of claim 11, wherein the compression element provides a force to the holding element to expel the second part of the multi-component blood sample therefrom.

15. The biological fluid separation and testing system of claim 11, wherein the compression element comprises a pair of rollers that squeeze the second part of the multi-component blood sample from the holding element.

16. The biological fluid separation and testing system of claim 11, wherein the filter comprises a lateral flow membrane.

17. The biological fluid separation and testing system of claim 11, further comprising a sample stabilizer disposed between the filter and the inlet port.

18. The biological fluid separation and testing system of claim 11, wherein the holding element comprises a wicking membrane.

19. The biological fluid separation and testing system of claim 11, further comprising a vent element disposed within the housing, the vent element in communication with the inlet port.

20. The biological fluid separation and testing system of claim 11, wherein the outlet port includes a septum transitionable between a closed position and an open position.

21. The biological fluid separation and testing system of claim 11, wherein the filter comprises a fibrous membrane.

* * * * *